United States Patent [19]

Wilms

[11] 4,439,026

[45] Mar. 27, 1984

[54] OPTICAL DEVICE WITH TWO REFLECTING SURFACES

[75] Inventor: Karl-Heinz Wilms, Emmering, Fed. Rep. of Germany

[73] Assignee: Optische Werke G. Rodenstock, Munich, Fed. Rep. of Germany

[21] Appl. No.: 315,067

[22] Filed: Oct. 26, 1981

[30] Foreign Application Priority Data

Oct. 24, 1980 [DE] Fed. Rep. of Germany ....... 3040214

[51] Int. Cl.³ .............................................. A61B 3/10
[52] U.S. Cl. .................................................. 351/219
[58] Field of Search ................................ 351/219, 160

[56] References Cited

U.S. PATENT DOCUMENTS 3,820,879 6/1974 Frisen .................................. 351/219

*Primary Examiner*—John K. Corbin
*Assistant Examiner*—Rodney B. Bovernick
*Attorney, Agent, or Firm*—Craig & Burns

[57] ABSTRACT

A contact glass with two reflecting surfaces for observing the chamber angle of a human eye in proximity of the iris, with a reflecting surface arranged laterally of the eye to be examined and a central reflecting surface to be located in the area of the common optical axis of the eye and of the axis of the contact glass; the path of observation rays is guided from the eye of the observer to the central reflecting surface and from the latter by way of the lateral reflecting surface into the interior of the eye whereby the lateral reflecting surface is so arranged to the common axis that its plane intersects the eye to be examined outside of the corneal area thereof and extends toward the eye to be examined up to a point to the rear of the center tangent of the eye abutment surface of the contact glass.

6 Claims, 1 Drawing Figure

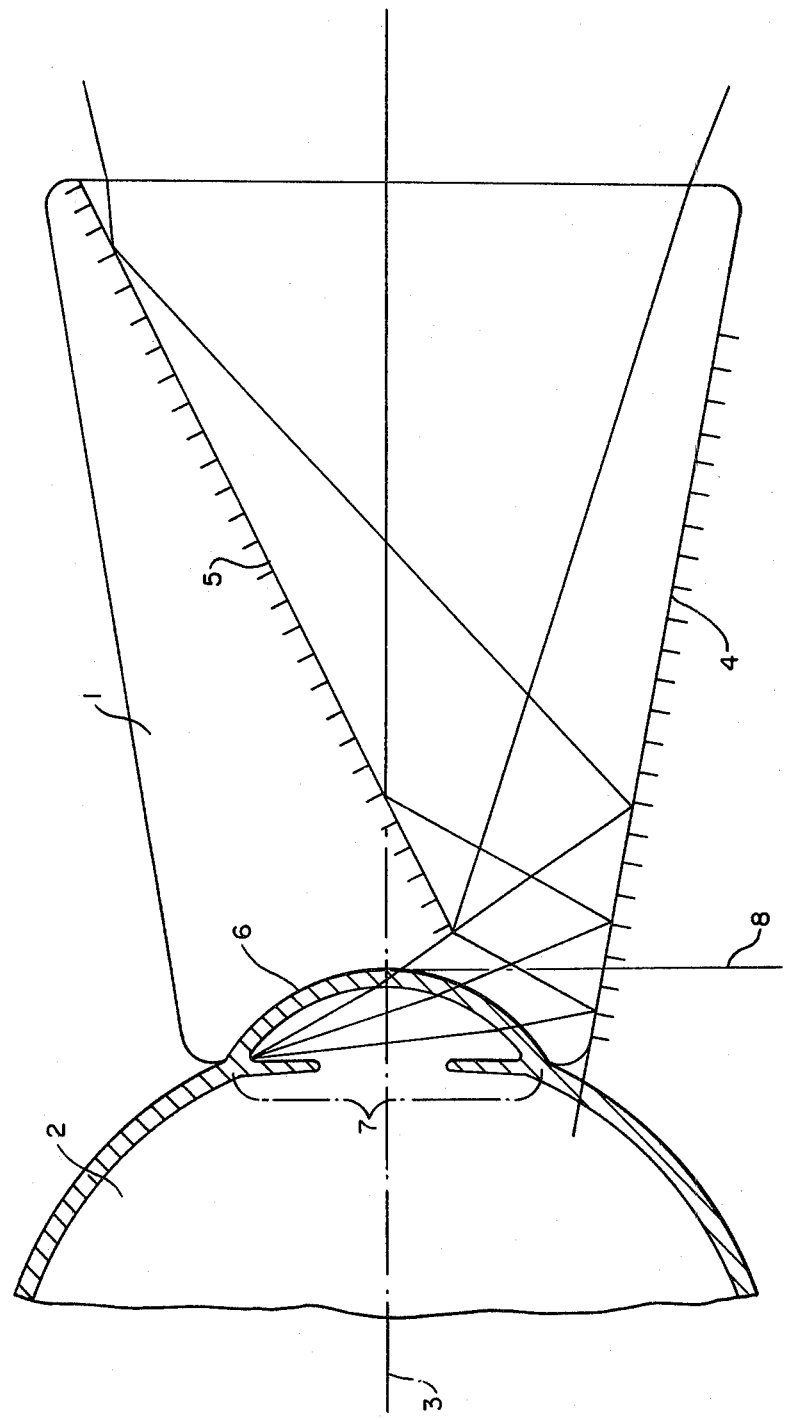

OPTICAL DEVICE WITH TWO REFLECTING SURFACES

The present invention relates to an optical device and, more particularly, to a double-reflecting contact glass provided with two reflecting surfaces for the observation of the interior of a human eye in the vicinity of the iris, with a lateral reflecting surface located near the eye to be examined and with a central reflecting surface located within the area of the common optical axis of the eye as well as the contact glass.

Contact glasses of the aforementioned type provided with two reflecting surfaces are generally used to observe the interior of the eye, whereby the direction of observation is to extend at as large as angle as possible to the optical axis of the eye to be examined. In particular, the chamber angle of the eye should be easily recognizable. Contact glasses of this type are, preferably, used in connection with slit lamps or similar goniometric devices.

A double-reflecting contact glass of the aforementioned type is disclosed, for example, in British Pat. No. 782,295, which includes a relatively small central reflecting surface and a lateral reflecting surface arranged forwardly of the center of the eye and at a small distance from the optical axis. This prior art contact glass produces a small field of view as well as poor image properties which result from the unfavorably large angle of incidence of the path of principal rays or viewing beam into the eye media and the refluctions resulting therefrom.

The aim underlying the present invention essentially resides in providing a contact glass having two reflective surfaces which has an enlarged field of view and produces the image of an interior of the eye which is largely free of reflections of the path of viewing rays at the outer surface of the cornea.

The underlying problems are solved in accordance with the present invention in that the lateral reflecting surface is so arranged to the common optical axis that its plane intersects the eye to be examined outside of the corneal area thereof and extends toward the eye to be examined up to a point to the rear of the center tangent of the eye abutment surface of the glass.

In accordance with further advantageous features of the present invention, the plane of the lateral reflecting surface intersects the eye to be examined at a distance of at least 7 mm from the common optical axis.

In accordance with still further features of the present invention, the central reflecting surface extends at least 20 mm to a rear from the boundary of the viewing light beam of the lateral reflecting surface.

The lateral reflecting surface which according to the present invention is extended close to the eye outside of the corneal area thereof, enables a viewing beam path entering the cornea at an acute angle outside the center area of the cornea and practically without reflection with a correspondingly completely satisfactory image.

The lateral reflecting surface extending in the direction toward the eye as compared to the prior art arrangements permits an advantageously large field of view in conjunction with an enlarged central reflecting surface.

Accordingly, it is an object of the present invention to provide an optimetric contact glass which avoids, by simple means, the aforementioned shortcomings and disadvantages encountered in the prior art.

Another object of the present invention resides in providing an optimetric contact glass which provides a large field of view.

Yet another object of the present invention resides in providing an optimetric contact glass having an enlarged central reflecting surface.

A further object of the present invention resides in providing an optimetric contact glass which enables the realization of an image of the eye interior which is free of reflections at an outer surface of the cornea of the eye.

These and other objects, features, and advantages of the present invention will become more apparent from the following description when taken in connection with the accompanying drawing which shows, for the purposes of illustration only, one embodiment in accordance with the present invention, and wherein:

The single FIGURE of the drawing is a partial schematical cross-sectional view of a double-reflecting contact glass in accordance with the present invention.

Referring now to the single FIGURE of the drawing, according to this figure, the double-reflecting contact glass 1 includes a lateral reflecting surface 4 and a central reflecting surface 5 as well as a concave abutment surface 6 adapted to be applied to an eye 2 to be examined. The path of the viewing rays or beam extends from the interior of the eye 2 by way of the lateral reflecting surface 4 and the central reflecting surface 5 to the observer. The lateral reflecting surface 4 is so located that its plane intersects the eye 2 outside of the corneal area 7 of the eye 2. With the human eye, a minimum distance of approximately 7 mm. results between the intersection and the optical axis 3. The forward area of the reflecting surface 4 which faces the eye 2, extends beyond the center tangent of the abutment surface 6. The position and dimension of the lateral reflecting surface 4 results in an extremely lateral passage of the viewing rays or beam through the corneal region 7 of the eye. This lateral passage has passage or penetration angles with extremely little reflection and thus provides high image quality. A large field of view desirable in addition to high image quality is achieved according to the present invention in that the center reflecting surface extends in the direction toward the eye 2 up to the path of viewing rays and, with a length of approximately 20 mm., extends extremely far to the rear.

The double-reflecting contact glass 1 may consist, for example, of an optically clear plastic element in which or at which the reflecting surfaces 4 and 5 are arranged. It is also possible for the reflecting surfaces 4 and 5 to be formed by the bonding planes of a correspondingly shaped multi-partite glass element. Similarly, it is possible for the reflecting surfaces 4 and 5 to be arranged freely in a housing.

While I have shown and described only one embodiment in accordance with the present invention, it is understood that the same is not limited thereto but is susceptible of numerous changes and modifications as known to one having ordinary skill in the art and I therefore do not wish to be limited to the details shown and described herein, but intend to cover all such modifications as are encompassed by the scope of the appended claims.

I claim:

1. A double-reflecting contact glass for the observation of the chamber angle of a common eye in proximity of its iris, comprising an eye abutment surface, a reflecting surface arranged laterally of the eye to be examined and a central reflecting surface provided within the area of the common optical axis of the eye as well as of the contact glass, the path of observation rays being guided from the eye of an observer to the central reflecting surface and from the latter by way of the lateral reflecting surface into the interior of the eye, characterized in that the lateral reflecting surface is so arranged with respect to the common optical axis that the plane of said reflecting surface intersects the eye to be examined outside of the corneal area thereof and extends in the direction toward the eye to be examined up to a location beyond a line tangent to the eye abutment surface and perpendicular to the optical axis of the eye.

2. A double-reflecting contact glass according to claim 1, characterized in that the plane of the lateral reflecting surface intersects the eye to be examined at a distance of at least 7 mm. from the common optical axis.

3. A double-reflecting contact glass according to claim 2, characterized in that the central reflecting surface extends rearwardly by at least 20 mm. from the boundary of the rays coming from the corneal area and impinging on the lateral reflecting surface.

4. A double-reflecting contact glass according to claim 3, wherein the plane of said lateral reflecting surface is located to one side of the optical axis and the plane of the central reflecting surface intersects said plane.

5. A double-reflecting contact glass according to claim 1, characterized in that the central reflecting surface extends rearwardly by at least 20 mm. from the boundary of the rays coming from the corneal area and impinging on the lateral reflecting surface.

6. A double-reflecting contact glass according to claim 1, wherein the plane of said lateral reflecting surface is located to one side of the optical axis and the plane of the central reflecting surface intersects said plane.

* * * * *